United States Patent [19]

Jolles et al.

[11] 4,001,395

[45] Jan. 4, 1977

[54] HYDROSOLUBLE EXTRACTS OF MYCOBACTERIA

[75] Inventors: Pierre Jolles, Paris; Danièle Migliore-Samour, Kremlin-Bicetre, both of France

[73] Assignee: Agence Nationale de Valorisation de la Recherche (ANVAR), Neuilly sur Seine, France

[22] Filed: Sept. 4, 1975

[21] Appl. No.: 610,477

Related U.S. Application Data

[63] Continuation-in-part of Ser. No. 371,658, June 19, 1973, abandoned.

[30] Foreign Application Priority Data

| | | |
|---|---|---|
| June 20, 1972 | France | 72.22208 |
| May 4, 1973 | France | 73.16130 |
| Sept. 4, 1974 | France | 74.30107 |

[52] U.S. Cl. .............................................. 424/92
[51] Int. Cl.$^2$ ................. A61K 39/00; A61K 39/02
[58] Field of Search ................................... 424/92

[56] References Cited

OTHER PUBLICATIONS

Chem. Abst. 8th Collective Index, vol. 66–75 (1967–1971) p. 19857s.

*Primary Examiner*—Sam Rosen
*Attorney, Agent, or Firm*—Burgess, Dinklage & Sprung

[57] ABSTRACT

Hydrosoluble extracts of mycobacteria suitable as immunological adjuvants are prepared. These extracts have a molecular weight between 3,500 and 30,000 and adjuvant, non-arthrogenic properties. The delipidated bacterial residues of mycobacteria are subjected to a mild extraction, then the so-obtained substance is isolated and purified by physicochemical methods, or the delipidated bacterial residues of mycobacteria are treated by means of pyridine optionally in the presence of acetic anhydride, then the obtained products are treated with ethanol or water, and the hydrosoluble substances are isolated and purified by physicochemical methods.

15 Claims, No Drawings

HYDROSOLUBLE EXTRACTS OF MYCOBACTERIA

This application is a continuation-in-part of application Ser. No. 371,658, filed June 19, 1973, now abandoned.

The present invention relates to hydrosoluble extracts of mycobacteria, their preparation and use as immunological adjuvants.

Certain mycobacterial preparation have the property of stimulating antibody formation [J. Freund, Adv. Tuberc. Res., 7, 130 (1956)] but have certain drawbacks such as the induction of experimental arthritis in the rat [B. H. Waksmann and coll., Immunology, 1, 54 (1968); R. G. White and coll., Immunology 7, 158 (1964)]. In these different active substances a polysaccharide (Poly) is linked to a peptidoglycane (PA).

More particularly, a ∓D wax" of Mycobacterium tuberculosis var-Hominis consists of a lipid portion linked by ester bonds to a hydrosoluble Poly-PA portion.

It is possible to obtain the hydrosoluble (Poly-PA) portion by chemical methods such as saponification [J. Asselineau, C. R. Acad. Sci., 229, 791 (1949)] or acetylation [P. Jollés and coll., Immunology, 14, 159 (1968)] or by biochemical methods which bring on the action of an enzyme [Adam A. and coll, Proc. Nat. Acad. Sci. USA 69, 851 (1972); Yanagida, Chem. Abstr., 76, 137 850 r(1972)]. All these hydrosoluble portions obtained by chemical or biochemical methods are not regularly active as immunological adjuvants. This irregular behaviour is notably due to more or less substantial modifications caused to sugars.

It has now been found, and it is this which is the object of the present invention, that starting with delipidated mycobacteria by treatments which do not destroy the sugars or which do not necessitate the use of enzymes, hydrosoluble products can be obtained which have an adjuvant and non-arthrogen activity.

The hydrosoluble extracts according to the present invention are substances, the molecular weight of which may be comprised between 3,500 and 30,000. In all these substances a nitrogenous portion, the structure of which may be compared with the structure of the peptidoglycane of the wall, is associated with reducing non-aminated sugars such as mannose, glucose, galactose, arabinose.

These substances may be obtained from delipidated bacterial residues of mycobacteria according to the method of A. Aebi et al. Bull. Soc. Chim. Biol. 35, 661 (1953):

either by mild extraction (homogenization in aqueous medium) followed by the application usually used of physico-chemical methods of isolation and purification, such as salting out, centrifugations, dialysis and chromatographies;

or by the action of pyridine optionally in the presence of acetic anhydride, followed by alcohol or water extractions and the application of the usually used methods of isolation and purification such as salting out, centrifugations, dialysis and chromatographies.

Thus the mild extraction provides a hyrosoluble extract which is called "Poly-PA" and which has the following characteristics:
appearance: pulverulent white powder (after freeze-drying)
composition:
a. amino acids (molecular ratio):alanine (3), glutamic acid (2), $\alpha,\alpha'$-diaminopimelic acid (2)
b. amino sugars (molecular ratio): N-acetylglucosamine (2), N-glycolylmuramic acid (2);and presence of N-acetylgalactosamine
c. non-amino reducing sugars:arabinose,galactose; and presence of mannose
d. lipids:less than 0.5%
molecular weight (calculated on the basis of three alanine residues per molecule) 14,000 ± 2,000
sedimentation constant $S_{20}$ O determinated with a Beckman apparatus) : 2

The treatment with pyridine in the presence of acetic anhydride provides a hydrosoluble substance designated as "Substance A" and having the following characteristics:
appearance: pulverulent yellow powder (after freeze-drying)
composition:
a. aminoacids (molecular ratio):alanine (3) glutamic acid (2), $\alpha$-$\alpha'$-diaminopimelic acid (2)
b. amino sugars (molecular ratio):N-acetylglucosamine (2),N-acetylmuramic acid (2)
c. non-amino reducing sugars:mannose, glucose, presence of arabinose:absense of galactose
d. absence of lipids
molecular weight (calculated on the basis of three alanine residues per molecule) 4,000 ± 200
Sedimentation constant $S_{20}$ (determinated with a Beckman apparatus):0.7

The treatment with pyridine alone provides two hydrosoluble substances:the one having a high molecular weight (26,500 ± 500) which is called "Substance B", the other of low molecular weight which is herein called "Substance C".

Substance C has the following characteristics:
appearance: white powder after freeze-drying
composition
a. amino acids (molecular ratio:alanine (3), glutamic acid (2),$\alpha,\alpha'$-diaminopimelic acid (2)
b. amino sugars (molecular ratio): N-acetylglucosamine (2), N-glycolylmuramic acid (2)
c. non-amino reducing sugars:arabinose, galactose, mannose.
molecular weight (calculated on the basis of three alanine residues per molecule) 6,000 ± 500.

The present invention is also relating to the purifying by chromatography of hydrosoluble extracts obtained by mild extraction or by the action of pyridine optionally in the presence of acetic anhydride as previously described.

According to one preferred embodiment of the present invention, it is possible to purify said extracts and notably hydrosoluble acetylated extracts, said purifying providing extremely purified extracts essentially consisting of tetrasaccharide-heptapeptide of mycobacteria cell wall, and being substantially free of non-aminated reducing sugars.

This preferred embodiment consists in purifying the products, obtained from delipidated bacterial residues of mycobacteria, by extraction with pyridine in the presence of acetic anhydride according to the process described hereinabove, by chromatography on an adsorbent of the weak anionic exchange agent type equilibrated at pH 7.7, by eluting with a pyridine-acetic acid buffer by changing the molarity of the buffer during elution in the manner described hereafter.

As an adsorbent useful for the embodiment of the process of the invention, it may be mentioned, for example, the product known by the trade name "DEAE-Biogel A" or any other adsorbent of the same type.

The elution is monitored by reading the optical density of the eluent by spectrophotometer at 220 mµ.

According to the invention, any pH 7.7. buffer may be used, but a pyridine buffer is particularly preferred since it is volatile and a salt removing step is thus unnecessary.

By eluting with a 0.01 N pH 7.7 pyridine-acetic acid buffer, a first peak is obtained at 220 mµ; the buffer of the elution is then replaced by a buffer solution of the same composition and the same pH but having a molarity of 0.2. Under these elution conditions, there is recovered the portion of the eluate showing a peak, also by optical reading, at 220 mµ; the product so recovered contains 2 molecules of N-acetylglucosamine (NAG), 2 molecules of N-acetylmuramic acid (NAM), 3 molecules of alanine (Ala), 2 molecules of glutamic acid (Glu) and 2 molecules of diaminopimelic acid (DAP) and is free of non-aminated reducing sugars, which corresponds to the molecular composition of the tetrasaccharide -heptapeptide the base structure of which may be represented as follows:

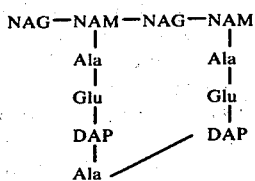

The hydrosoluble extract so purified is, like the starting material biologically active as adjuvant and immunostimulant and are included within the scope of the present invention.

The mycobacteria which may be used for carrying out the process according to the invention are the virulent or non-virulent mycobacteria of human or non-human origin, in which the existence of a "D wax" has been indicated. Among the mycobacteria which may be used there may be mentioned: *Mycobacterium tuberculosis*, var. hominis Peurois strain, Test-strain, Brevannes strain or H37Ra strain, *Mycobacterium kansasii*, *Mycobacterium tuberculosis*, var. bovis, LA, BB and Behring strains.

In the present disclosure the expression "hydrosoluble extracts" represents the hydrosoluble substances obtained by mild extraction or by the action of pyridine optionally in the presence of acetic anhydride as well as the highly purified substances obtained according to the pyrifying process described hereinabove or to a similar pyrifying process.

The hydrosoluble extracts of the present invention have an adjuvant and non arthrogen activity.

The adjuvant power is determined in the Hartley strain guinea pig according to the principle of the method of R. G. White and coll., Immunology, 7,158 (1964) and the anthrogen and protective powers according to the methods described by F. Bonhomme, C. R. Acad. Sci., Series D, 263,1,422 (1966) and C. R. Acad. Sci., Series D, 265,211 (1967).

In the guinea pig, the hydrosoluble substances according to the invention provide an increase of the antibodies level at doses higher than, or equal to, 0.1 mg by introdermic injection.

The adjuvant power is also determined by production of circulating antibodies in the rabbit, the antigen used being human influenza virus B/Massachusetts/3/66 according to the procedure described in the article by G. H. WERNER et al. in C. R. Acad. Sc. Paris t. 278 (Feb. 4, 1974) Series D, p. 789.

The new products according to the invention can be used in human or veterinary therapy to enhance the resistance to infections of viral or bacterial origin. They provide an increase of the antibodies formation useful to control pathogenic organisms and they may be associated with the administration of vaccines to ensure the maximum reaction of antibodies.

The present invention also relates to pharmaceutic compositions containing at least one hydrosoluble substance according to the invention associated with one or more compatible diluents or adjuvants and optionally with other medicaments such as antibiotics, lipids, decongestive agents and vaccines. The content of the product according to the invention in said compositions is generally higher than 0.1%.

Said compositions may be administered orally, rectally, parenterally way or as aerosols.

In human therapy, the doses depend on the desired effect. They may be in the range of 10 to 50 mg per day for an adult.

The following examples, given without limitation, illustrate the preparation of hydrosoluble substances according to the invention.

EXAMPLE 1

100 g of bacterial residues obtained from *Mycobacterium tuberculosis* var.hominis, Peurois strain, according to the method of A. Aebi et al. are ground and homogenized in 500 cm³ of water by means of a grinder (Vetra-Turrax).

After stirring during 5 hours at 20° C and centrifugation for 30 minutes at 4° C (4000 r.p.m.) the supernatant layer is heated to 80° C. Ammonium sulfate is then added to obtain a 40% saturated solution. After 12 hours at 4° C and centrifugation for 30 minutes a precipitate ($P_{40}$) is obtained.

Ammonium sulfate is added to the supernatant layer to obtain a 70% saturation for 30 minutes. Under the same conditions a precipitate ($P_{70}$) is obtained. The $P_{40}$ and $P_{70}$ precipitates and the last supernatant layer obtained ($S_{70}$) are then dialyzed separately against distilled water. The various solutions which do not dialyse are freeze-dried. There is thus obtained 1.2g of fraction $P_{40}$, 1.4g of fraction $P_{70}$ and 0.9g of fraction $S_{70}$ containing the major portion of the biologically active substance.

This latter fraction is purified by chromatography on DEAE-cellulose equilibrated with a 0.05 M pH 7 phosphate buffer, eluting with a 0.05 M pH 3 sodium citrate buffer. 400 mg purified Poly-PA are thus obtained.

After filtration on Biogel P10, the eluting with water, 150 mg highly purified Poly-PA is obtained.

The compositions after the Poly-PA obtained is determined as follows:

the amino-acid and amino-sugar composition is determined by means of an autoanalyzer (Technicon type) after total hydrolysis with 6N hydrochloric acid at 110° C for 18 hours and 6 hours respectively, the non-amine neutral sugar composition is determined after hydrolysis with 2N hydrochloric acid for 2 hours at 110° C, qualitatively by paper chromatography [Whatman N°1; solvent:butanol-pyridine-water (6-4-3) by volume)] and quantitatively by the means of a sugarsautoanalyzer (Technicon type).

lipid determination is effectd by their layer chromatography on silica gel after total hydrolysis and ether extraction.

The purified Poly-PA previously obtained has the following characteristics:
appearance: pulverulent white powder
composition
a. amino acids (molecular raio):alanine (3) glutamic acid (2),α-α'diaminopimelic acid (2),
b. amino sugars (molecular ratio:N-acetyl-glucosamine (2),N-glycolylmuramic acid (2,presence of N-acetylgalactosamine,
c. non amine reducing sugars:arabinose, galactose; presence of mannose
d. lipids: less than 0.5% the aminoacid content is 6.2%, the aminosugar content is 7–8% and the rest consists of non amino reducing sugars.

molecular weight (calculated on the basis of 3 alanine residues per molecule):14,000 ± 2000.

sedimentation constant:2.

EXAMPLE 2

20g of bacterial residues obtained from *Mycobacterium tuberculosis*, var.hominis, strain $H_{37}Ra$ in 250 cm$^3$ of a pyridine-acetic anhydride mixture (3-2 by volume) is stirred for 36 hours at 28° C. Then 2500 cm$^3$ of ethyl alcohol is added and stirred for one night. The insoluble portion is separated by centrifugation (4,000 r.p.m.). The supernatant layer is concentrated to dryness under low pressure. The residue is added to 200 cm$^3$ of water. The water-insoluble portion is separated by centrifugation (4,000 r.p.m.). The supernatant layer is filtered through a Biogel P10 column.100 mg of hydrosoluble substance A are obtained after freeze-drying.

The composition of substance A is determined in the following manner:

the aminoacid and aminosugar composition is determined by means of an autoanalyzer (Technicon type) following total hydrolysis with 6N hydrochloric acid at 110° C for 18 hours and 6 hours respectively. the non amino sugar composition is determined, after hydrolysis with 2N hydrochloric acid for 2 hours at 110° C, qualitatively by paper chromatography [Whatman N°1, solvent:butanol-pyridine-water(6-4-3) by volume)] and quantitatively by gas chromatography with a sugar autoanalyzer, after methylation and silylation using a HEWLETT-PACKARD chromatograph.

lipid determination is effected by thin layer chromatography on silica gel after total hydrolysis and ether extraction.

The hydrosoluble substance A previously obtained has the following characteristics
appearance: pulverulent yellow powder
composition
a. amino acids (molecular ratio): alanine (3), glutamic acid (2), α,α'-diaminopimelic acid (2),
b. amino sugars (molecular ratio): N-acetylglycosamine (2), N-acetylmuramic acid (2)
c. non amino reducing sugars:mannose, glucose; presence of arabinose,absence of galactose.
d. absence of lipids the content of aminoacids is 31 ± 5%, and the content of amino-sugars is 25 ± 5%, the rest consisting of non-amino reducing sugars (11%) and acetylated functions fixed to the amino or non-amino reducing sugars by acetylation molecular weight (calculated on the basis of 3 alanine residues per molecule):4,000 ± 200 sedimentation constant:0,7

EXAMPLE 3

20g of bacterial residues obtained from *Mycobacterium tuberculosis* var.hominis, Test strain, in 250 cm$^3$ of pyridine are stirred for 36 hours at 28° C. Then 2500 cm$^3$ of ethyl alcohol are added and the whole is stirred again for one night. The insoluble portion, which is separated by centrifugation, is homogenized in 100 cm$^3$ of water by means of a grinder (Ultra-Turrax).

After stirring for 48 hours at 40° C and centrifugation for 30 minutes at 4° C (4000 r.p.m.) the supernatant layer is heated to 80° C. Ammonium sulfate is then added in order to obtain a 40% saturated solution. After 12 hours at 4° C and centrifugation for 30 minutes, a precipitate ($P_{40}$) is obtained.

Ammonium sulfate is added to the supernatant layer in order to obtain a 70% saturated solution.

After 12 hours at 4° C and centrifugation for 30 minutes under the same conditions a precipitate ($P_{70}$) is obtained.

The $P_{40}$,$P_{70}$ precipitates and the last supernatant layer obtained ($S_{70}$) are then dialyzed separately against distilled water. The various solutions which do not dialyze are freeze-dried. A fraction ($P_{40}$) a fraction $P_{70}$ and 0.8g of fraction $S_{70}$ containing the major portion of the biologically active substances are thus obtained.

Said last fraction is purified by chromatography on DEAE-cellulose equilibrated with a 0.05 M pH 7 phosphate buffer by eluting with an 0.05 M pH 3 sodium citrate buffer. After dialyzing and freeze-drying the corresponding fractions,0.15g hydrosoluble substance B and 0.1g hydrosoluble substance C are obtained.

The composition of substance C is determined according to the methods described in example 2.

The hydrosoluble substance C previously obtained has the following characteristics:
appearance: white powder after freeze-drying.
composition:
a. amino acids (molecular ratio):alanine (3), glutamic acid (2), α-α'-diaminopimelic acid (2),
b. amino sugars (molecular ratio):N-acetylglycosamine (2),N-glycolylmuramic acid (2),
c. non amino reducing sugars:arabinose, galactose, mannose,
d. absence of lipids the aminoacid content is 16 ± 3%, the amino sugar content is 16 ± 3%. the rest consists of non amino reducing sugars.

molecular weight (calculated on the base of 3 alanine residues per molecule):6,000 ± 500.

EXAMPLE 4

In this example, the substance A obtained according to above example 2 was purified.

A "DEAE-Biogel A" column (50 × ½ cm) was used, said column being equilibrated with a 0.01 N pH 7.7 pyridine-acetic acid buffer. The column was charged with 50 mg of the substance A and the eluting was effected with a pH 7.7 pyridine-acetic acid buffer;1.5 ml fractions of the eluate were recovered and said fractions were analyzed by optical reading at 220 mµ; a first peak was thus located at 200 mµ among the 1.5 ml fractions after having eluted about 25 to 40 ml of the product;the first buffer was then replaced by a second one having the same value of pH and the same composition but a molarity of 0.2. Under these conditions, a second peak at 220 mµ was located after about 30 ml of the product had been eluted.

The product thus located was analyzed;analyses showed that this compound had the following composition, the figures in brackets showing the molecular ratios of amino-acids and amino-sugars:

alanine (3), glutamic acid (2), diaminopimelic acid (2) N-acetylglucosamine (2) and N-acetylmuramic acid (2). This product therefore consists essentially of the tetrasaccharide heptapeptide of the cell wall. It is free of non-aminated reducing sugars.

EXAMPLE 5

The same procedure as described in example 4 was employed using,as starting substances, "substances A" obtained from bacterial residues derived from the mycobacteria mentioned below by extraction with pyridine in the presence of acetic anhydride;substances consisting essentially of the tetrasaccharide-heptapeptide of the cell wall were thus obtained.

The following mycobacteria were used: *Mycobacterium tuberculosis* var.hominis, Peurois strain, Test strain or Brevannes strain;Behring strain (var.bovis); atypical strain (kanasii n°1).

What we claim is:

1. A process for the preparation of hydrosoluble extracts of delipidated mycobacteria, said extracts having a molecular weight in the range of about 3,500 to 20,000, said process consisting essentially of subjecting the bacterial residues of said delipidated mycobacteria to a treatment with pyridine, extracting with a solvent selected from the group consisting of alcohol and water, and isolating hydrosoluble substances from the extract by physicochemical means.

2. The process of claim 1, wherein the treatment with pyridine is carried out in presence of acetic anhydride.

3. The process of claim 1, wherein the bacterial residues of delipidated mycobacteria used as starting material are obtained from mycobacteria containing D-wax.

4. The process of claim 3, wherein said mycobacteria are selected from the group consisting of Mycobacterium tuberculosis, var.hominis, Peurois strain,Test-Strain, Brevannes strain or $H_{37}R_a$ strain,Mycobacterium kansasii, Mycobacterium tuberculosis, var.-bovis, LA,BB and Behring strains.

5. Hydrosoluble extracts of delipidated mycobacteria obtained from mycobacteria containing "D wax", said extracts having a molecular weight in the range about 3,500 to 30,000 and having adjuvant and nonarthrogen properties and prepared by the process of claim 1.

6. The hydrosoluble extract of claim 5 having the following properties:
appearance:pulverulent yellow powder (after freeze-drying)
composition:
 a. amino acids (molecular ratio):alanine (3) glutamic acid (2), α,α'-diaminopimelic acid (2),
 b. amino sugars (molecular ratio):N-acetylglucosamine (2),N-acetylmuramic acid (2),
 c. non-amino reducing sugars:mannose,glucose;-presence of arabinose; absence of galactose,
 d. absence of lipids molecular weight (calculated on the basis of three alanine residues per molecule)4,000 ± 200
sedimentation constant $S_{20}$ = 0,7.

7. The hydrosoluble extract of claim 5 having the following properties:
appearance:white powder after freeze-drying
composition:
 a. amino acids (molecular ratio):alanine (3) glutamic acid (2),α,α'-diaminopimelic acid (2)
 b. amino sugars (molecular ratio):N-acetylglucosamine (2)N-glucolylmuramic acid (2),
 c. non amino reducing sugars:galactose, mannose, arabinose
molecular weight (calculated on the basis of three alanine residues per molecule) 6,000 ± 500.

8. Pharmaceutical compositions which contain an effective amount of hydrosoluble extract obtained by the process of claim 1, in association with a pharmaceutically acceptable diluent or adjuvant.

9. A process for the preparation of acetylated hydrosoluble extracts of delipidated mycobacteria, said extracts having a molecular weight in the range of about 3,500 to 20,000, said process consisting essentially of subjecting bacterial residues of said delipidated mycobacteria to treatment with pyridine in presence of acetic anhydride, adding alcohol, separating the alcohol solution from the undissolved residue, removing the solvent from the alcohol solution to leave a dry material and extracting said dry material with water to form a solution of active acetylated material.

10. The process of claim 9, wherein said active acetylated material is purified by chromatography on an adsorbent of the weak anionic exchange agent type, equilibrated at pH 7.7 by eluting with a pH 7.7 buffer and by modifying the molarity of the buffer during eluting.

11. The process according to claim 10, wherein the eluting is carried out with a pyridine-acetic acid buffer.

12. The process according to claim 10, wherein the adsorbent is the product known under the trade name "DEAE Biogel A", the said adsorbent is equilibrated at pH 7.7 with a pyridine-acetic acid buffer, the eluting is effected with the same buffer having a molarity of 0.01 until a peak at 220 mµ is obtained by optical reading and is then effected with the same buffer having a molarity of 0.2 until a peak at 220 mµ is obtained, said hydrosoluble extract being recovered during the second eluting.

13. The process of claim 12, wherein a hydrosoluble extract highly purified is obtained, said extract essentially consisting of an acetylated tetrasaccharideheptapeptide free of non-aminated reducing sugars and having the following composition, the figures in brackets indicating the molecular ratios of the amino acids=
Alanine (3)
Glutamic acid (2)
Diaminopimelic acid (2)
N-acetylglucosamine (2)
N-acetylmuramic acid (2).

14. A process for the preparation of a hydrosoluble extract having the following properties:
appearance:pulverulent yellow powder (after freeze-drying)
composition:
 a. amino acids (molecular ratio):alanine (3) glutamic acid (2),α,α'-diaminopimelic acid (2),
 b. amino sugars (molecular ratio); N-acetylglucosamine (2),N-acetylmuramic acid (2), c. non amino reducing sugars:mannose, glucose; presence of arabinose; absence of galactose,
d. absence of lipids
molecular weight (calculated on the basis of three alanine residues per molecule) 4,000 ± 200
sedimentation constant $S_{20} = _{0.7}$ said process consisting of treating the delipidated bacterial residues of mycobacteria with pyridine-acetic anhydride mixture, after which ethyl alcohol is added, the alcohol-insoluble fraction is extracted with water, then the hydrosoluble extract obtained is isolated and purified by chromatography.

15. A process for the preparation of a hydrosoluble extract having the following properties:
appearance: white powder after freeze-drying
composition:
a. amino acids (molecular ratio):alanine (3) glutamic acid (2) $\alpha,\alpha'$-diaminopimelic acid (2)
b. amino sugars (molecular ratio):N-acetylglucosamine (2), N-glucolylmuramic acid (2)
c. non amino reducing sugars:galactose, mannose, arabinose molecular weight (calculated on the basis of three alanine residues per molecule) 6,000 ± 500, said process consisting of treating the delipidated bacterial residues of mycobacteria with pyridine, after which ethyl alcohol is added, the alcohol-insoluble fraction is extracted by homogenization in an aqueous medium, then, after centrifugation, two salting out steps are effected on the hydrosoluble fraction by means of ammonium sulfate, each followed by centrifugation, the obtained supernatant layer is dialysed against distilled water and finally the hydrosoluble extract is separated, isolated and purified by chromatography.

* * * * *

UNITED STATES PATENT AND TRADEMARK OFFICE
CERTIFICATE OF CORRECTION

PATENT NO. : 4,001,395
DATED : January 4, 1977
INVENTOR(S) : Pierre Jolles et al It is certified that error appears in the above-identified patent and that said Letters Patent are hereby corrected as shown below:

Page 1 of Patent - item [63], cancel "abandoned" and substitute -- Patent No. 3,956,481 --.

Signed and Sealed this

Eighteenth Day of April 1978

[SEAL]

Attest:

RUTH C. MASON
Attesting Officer

LUTRELLE F. PARKER
Acting Commissioner of Patents and Trademarks